United States Patent [19]

Mitta et al.

[11] Patent Number: 5,217,880
[45] Date of Patent: Jun. 8, 1993

[54] L-FUCOSE DEHYDROGENASE GENE, MICROORGANISM HAVING SAID GENE AND PRODUCTION OF L-FUCOSE DEHYDROGENASE BY THE USE OF SAID MICROORGANISM

[75] Inventors: Masanori Mitta, Tsuzuki; Takeshi Sakai, Hirosaki; Hirokazu Kotani, Moriyama; Ikunoshin Kato, Uji, all of Japan

[73] Assignee: Takara Shuzo Co., Ltd., Kyoto, Japan

[21] Appl. No.: 855,793

[22] Filed: Mar. 23, 1992

[30] Foreign Application Priority Data

Mar. 29, 1991 [JP] Japan .................................. 3-089184

[51] Int. Cl.$^5$ .................... C12P 21/06; C12N 1/20; C12N 9/04; C12N 15/00
[52] U.S. Cl. ............................. 435/69.1; 435/252.33; 435/190; 536/23.2
[58] Field of Search ................. 435/69.1, 252.33, 190; 536/27

[56] References Cited

U.S. PATENT DOCUMENTS 4,927,753  5/1990  Sakai et al.

OTHER PUBLICATIONS

*J. Biochem.*, Endo et al., 86:1559–1565 (1979).
*Agricultural and Biological Chemistry*, 53(6) 1493–1501 (Jun. 1989).
"World Patents Index Latest", Week 9048, JP-A 2257881 (Derwent Publications, Ltd.) (Oct. 1990).
"World Patents Index Latest", Week 8615, JP-A 61040792 (Derwent Publications, Ltd.) (Feb. 1986).
Chemical Abstracts, 112(13) 114617t (Mar. 26, 1990).
"World Patents Index Latest", Week 8733, JP-A 62155085 (Derwent Publications, Ltd.) (Jul. 1987).

*Primary Examiner*—Robert A. Wax
*Assistant Examiner*—Keith D. Hendricks
*Attorney, Agent, or Firm*—Wenderoth, Lind & Ponack

[57] ABSTRACT

There is provided an isolated gene from Arthrobacter oxidans encoding L-fucose dehydrogenase. Also provided are a process for producing L-fucose dehydrogenase by culturing *E. coli* containing a plasmid that carries the gene encoding the enzyme.

3 Claims, 1 Drawing Sheet

F I G. 1

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: No     ( i v ) ANTI-SENSE: No     ( v ) FRAGMENT TYPE:

( v i ) ORIGINAL SOURCE:
        ( A ) ORGANISM:

( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION: /note="1-20 E probe"

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:1:

TGGGGNGCNG GNATGAAYCA          20

( 2 ) INFORMATION FOR SEQ ID NO:2:

( i ) SEQUENCE CHARACTERISTICS:
                    ( A ) LENGTH: 7 amino acid residues
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL:

( i v ) ANTI-SENSE:

( v ) FRAGMENT TYPE: internal fragment ( v i ) ORIGINAL SOURCE:
                    ( A ) ORGANISM: Arthrobacter Oxidans
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:

( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:2:

```
Trp Gly Ala Gly Met Asn Gln
 1               5
```

( 2 ) INFORMATION FOR SEQ ID NO:3:

( i ) SEQUENCE CHARACTERISTICS:
        ( A ) LENGTH: 2682 Base Pairs
        ( B ) TYPE: nucleic acid
        ( C ) STRANDEDNESS: double
        ( D ) TOPOLOGY: linear     ( i i ) MOLECULE TYPE: genomic DNA     ( i i i ) HYPOTHETICAL:

( i v ) ANTI-SENSE:

( v ) FRAGMENT TYPE:

( v i ) ORIGINAL SOURCE:
        ( A ) ORGANISM: Arthrobacter Oxidans
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note="844-1809 E CDS"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

```
GGATCCCGCC  GGGCTCGACT  ACACCTGGCT  GGAGGATGCG  CCCACCCTGA  ACAAGCCATT      60
CCTTCCCCAA  GACCTCCCGC  ATACCGGGGC  AAACACCCGT  GCTGCCGTTT  TTGTCCAGGC     120
CGACTGCCGT  AATGACCAAG  CCCTGAAGGA  AGTGGACTGG  GTATCGGGCC  TGCACGCTGG     180
CTGGCCGCAG  CTGGCGGGGA  TTGTGGCCTT  CGCCCCCATC  AGCCGCGGTG  ACGCGGTAGC     240
```

```
GGAGGACCTG GACCAGCTGC TGGAACGCCC GCTGGTACGG GGCATCAGGC AGCTGTTCCA    300
GGACCGGGAC GCATCATTCA TGGTGGACCC CAAGACGCTG GCCGGTGCAC GGCAGGTGGC    360
GGCGTCCAGG CTGGTATTCG ATGCGTGCAT CCGTGCCGGA CAGCTGCCGG CCCTGGCGGA    420
ATTTGCCTGC CGCGTCCCCG AGCTGCTGAT TGTGTTGGAC CACATGGGCA AGCCCCCTCT    480
GGCCAGCGGC GACCTGGCGA GTTGGAGCAA GGGGATGCGC GAACTCGCCG GCACCCCAA    540
CGTCACCGTC AAGATTTCCG GGGCCGGCGC GGAACCGACC CGCAGCGTCC GCTGGCGCCC    600
CAGGCACAGC CGTCATTCAT GAAACACTGC GGCTCTTCGG TGCGGAGGCT GCATGATCGG    660
CAGCGACTTT CCCGTCTCGA TGACAAGCCC TGCCGCTTAC GAGGACTGGA TCACCATTGT    720
GGAAGAGTCG ATGGCAGGTG CTTCCGACGG CGAGCGCGCC AGCTCAACGC ACCGGACGGC    780
AGCCCGCGTC TACCAGCTCA CGGAAGAGCC AGGACAGGCC CCCAACCAGG AGAAAGACTG    840
ATC ATG CAA GAA ACG CGC ACC ATC CCC GGC ACG GAC GTC CTG CTG          885
    Met Gln Glu Thr Arg Thr Ile Pro Gly Thr Asp Val Leu Leu
    1               5                   10
CCG GTG CTC GGC TTC GGG GGC GCC CCC ATC GGC AAC CTC TAC CGG          930
Pro Val Leu Gly Phe Gly Gly Ala Pro Ile Gly Asn Leu Tyr Arg
15              20                  25
CAG GTC CCG GAG CAG GAA GCG GTC GAC GCC GTC AGC GCG GCC TGG          975
Gln Val Pro Glu Gln Glu Ala Val Asp Ala Val Ser Ala Ala Trp
30              35                  40
GAG GGC GGC GTC CGC TAT TTC GAT ACC GCG CCG CAC TAC GGG CTG         1020
Glu Gly Gly Val Arg Tyr Phe Asp Thr Ala Pro His Tyr Gly Leu
45              50                  55
GGG CTC TCG GAA CGC CGC ATG GGC GCC GCG CTC GCA GGG CAG GAC         1065
Gly Leu Ser Glu Arg Arg Met Gly Ala Ala Leu Ala Gly Gln Asp
60              65                  70
CGC GAC AGT TAC GTG CTC AGC ACG AAG ATC GGG CGG CTC CTG CGC         1110
Arg Asp Ser Tyr Val Leu Ser Thr Lys Ile Gly Arg Leu Leu Arg
75              80                  85
CCC AAC CCG TCC CCG CAG GGC AAG GAC ACC GAG GGC TTC GAC GTC         1155
Pro Asn Pro Ser Pro Gln Gly Lys Asp Thr Glu Gly Phe Asp Val
90              95                  100
CCG GAC GAC CTC ATC CGG GTC CGC GAC TAC TCC CGC GAC GGG GTG         1200
Pro Asp Asp Leu Ile Arg Val Arg Asp Tyr Ser Arg Asp Gly Val
105             110                 115
CTG CGC TCC ATC GAG GAA AGC CTG CAG CGG CTG GGG ACC GAC CGG         1245
Leu Arg Ser Ile Glu Glu Ser Leu Gln Arg Leu Gly Thr Asp Arg
120             125                 130
ATC GAC ATC GTC TAC ATC CAC GAC CCT GAC GAC TAC TGG ACC GAG         1290
Ile Asp Ile Val Tyr Ile His Asp Pro Asp Asp Tyr Trp Thr Glu
135             140                 145
GCC GTG GAG GGC GCC GCC CCG GCG CTG TCC GCC CTG CGG GAC GAA         1335
Ala Val Glu Gly Ala Ala Pro Ala Leu Ser Ala Leu Arg Asp Glu
150             155                 160
GGG GTC ATC AGG GCC TGG GGC GCA GGC ATG AAC CAA TCC GGG ATG         1380
Gly Val Ile Arg Ala Trp Gly Ala Gly Met Asn Gln Ser Gly Met
165             170                 175
CTC CAC AGG TTC ATC ACC GAA ACG GAC ATT GAC GTT GTC ATG CTG         1425
Leu His Arg Phe Ile Thr Glu Thr Asp Ile Asp Val Val Met Leu
180             185                 190
GCC GGC CGG TAC ACG CTC CTG GAG CAG GGT GCA GCA CAG GAC CTG         1470
Ala Gly Arg Tyr Thr Leu Leu Glu Gln Gly Ala Ala Gln Asp Leu
195             200                 205
CTT CCT GCC TGC CTG GAG CGC GGG GTT GGC GTG GTG AAC GTC GGT         1515
Leu Pro Ala Cys Leu Glu Arg Gly Val Gly Val Val Asn Val Gly
210             215                 220
GTC TTC AAT TCG GGC CTG CTG TCC AAG GAG CGG CCC GCG GCC AAC         1560
Val Phe Asn Ser Gly Leu Leu Ser Lys Glu Arg Pro Ala Ala Asn
225             230                 235
GCC ACC TAC AAC TAC GCC CCG GCC CCG CAG GAA CTG CTG GAC AGG         1605
Ala Thr Tyr Asn Tyr Ala Pro Ala Pro Gln Glu Leu Leu Asp Arg
240             245                 250
GCC AAC CTG CTG GCA GAC GTC TGC GAA TCC CAC GGC ACC ACG CTG         1650
Ala Asn Leu Leu Ala Asp Val Cys Glu Ser His Gly Thr Thr Leu
255             260                 265
CCC GCC GCC GCC CTC CAC TTC CCC TAC CAG CAC CCC GCC GTC ACC         1695
Pro Ala Ala Ala Leu His Phe Pro Tyr Gln His Pro Ala Val Thr
270             275                 280
AGC GTT GTC CTT GGC ATG CGG ACG CCG GCA CAG GTG AAG CAA AAC         1740
Ser Val Val Leu Gly Met Arg Thr Pro Ala Gln Val Lys Gln Asn
285             290                 295
CTG GAC CTC GCC TCG CAG ACC GTC CCG GAC CAG CTG TGG GCT GAC         1785
Leu Asp Leu Ala Ser Gln Thr Val Pro Asp Gln Leu Trp Ala Asp
300             305                 310
CTG CGG GAC CGC GGA CTG ATC TCC TAAAAAGCAC AATCACGTAC               1829
Leu Arg Asp Arg Gly Leu Ile Ser
315             320
AACCAAGAAA AGAAGAAACG AATGCAATTT GCACGCATAG GTGCCCCCGG CAAGGAAGTC  1889
CCCGCCCTGC TGCACGGGAA GAAGTACTAC TCCCTGGAAC ACGTGGCCCG GGACATCGAC  1949
GCCGATTTCT GGGAATCCGA CGGTCCCGGC CCCGCGGCAA CGGCGCTGGC CGCGGGGGAA  2009
CTGGCGGAAC TGCGTGGACG GCGCCCGGAT CGGCGCTCCG ATCGCCAGGC CGTCCTCCGT  2069
GATCTGTGTG GGCATGAACT ACGCCGCGCA CGCCGCCGAG TCGGGCTCTG CTCCCCCTAC  2129
CGTGCCCATC ATCTTCCACA AGGCCCCCAA CACCGTGGCT GGCCCGTTCG ATGCCGTGGC  2189
```

```
GATTCCGCGT GGTTCCACGA AGACCGACTG GGAAGTCGAA CTGGGCGTGG TCATCGGCCG    2249
GCGCGCCTCG TACCTGGAAT CCCCTGCGCA GGCCCGGGAC TATATCGCCG GCTACGTCAC    2309
CGTCAATGAC CTGTCCGAGC GCACGTTCCA GCTGGAAGTG TCCGGAGGCC AATGGTCCAA    2369
GGGAAAGAGC TGTGCAGGAT TTTGTCCCAC CGGACCGTAC CTGGTCACCC CCGATGAGGT    2429
GGATGCCGGG GACCTTCGGC TGCGCAGCTG GGTCAACGGC GAAATCCGCC AGGACTCCAG    2489
CACCCGGGAC CTGATCTTCG GTGTGGAGCA GGTGATCTAT GACCTGAGCC AGTTCCTTGT    2549
CCTTGAACCG GGTGACCTGG TCTGCACCGG CACCCCGGAG GGAGTAGCCC TGTCCGGCCG    2609
CTTCCCGTAC CTGAAGGCCG AGACGTCGT CGACATCGAA GTGGCGGGAC TGGGCCGCCA    2669
GCGCCAGGAA TTC                                                      2682
```

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear     ( i i ) MOLECULE TYPE: genomic DNA     ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note="1-7 E M13mp19
                DNA and 8-39 E Arthrobacter oxidans genomic DNA"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:4:

```
GAATTCGGGA CAGGCCCCCA ACCAGGAGAA AGACTGATC                           39
```

( 2 ) INFORMATION FOR SEQ ID NO:5:

( i ) SEQUENCE CHARACTERISTICS:
        ( A ) LENGTH: 14 amino acid residues
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:5:

Met Glu Phe Gly Thr Gly Pro Gln Pro Gly Glu Arg Leu Ile
1               5                   10

L-FUCOSE DEHYDROGENASE GENE, MICROORGANISM HAVING SAID GENE AND PRODUCTION OF L-FUCOSE DEHYDROGENASE BY THE USE OF SAID MICROORGANISM

This invention relates to a DNA that carries genetic information for the production of L-fucose dehydrogenase, to new microorganisms (particularly, new strains of *Escherichia coli*) harboring a plasmid into which said DNA has been integrated, and to a process for producing L-fucose dehydrogenase by using said new microorganism.

L-fucose is found at the non-reducing ends of various sugar chains in the body, where it influences the antigenicity of the sugar chain, and participates in the transmission of information; it is also found in structural sugars of mucus of the stomach and intestines and of fucoidan of seaweeds.

A number of complexes with L-fucose are at high concentrations in the serum of patients with malignancies (Cancer Research, 37, 4101–4103, 1977), and the level of urinary free L-fucose is high in patients with cirrhosis or malignant disease (Clinical Chemistry, 36, 474–476, 1990). By the measurement of L-fucose in a variety of samples such as urine, serum, and mucus, it is possible to obtain information about changes in the metabolism of L-fucose in the body and in certain disease. L-fucose can be assayed biochemically by HPLC and by enzymatic methods. The most rapid and simple method is an enzymatic method that uses L-fucose dehydrogenase.

L-fucose dehydrogenases have been obtained from *Pseudomonad* (Journal of Biological Chemistry, 240, 4493–4497, 1965), porcine liver (Journal of Biological Chemistry, 244, 4785–4792, 1969), Pseudomonas (Agricultural and Biological Chemistry, 39, 2227–2234, 1975), sheep liver (Archives of Biochemistry and Biophysics, 139, 83–86, 1970), rabbit liver (Journal of Biochemistry, 86, 1559–1565, 1979), Pullularia (Canadian Journal of Microbiology, 30, 753–757, 1984), Corynebacterium (U.S. Pat. No. 4,927,753), and again Pseudomonas (Agricultural and Biological Chemistry, 53, 1493–1501, 1989). L-fucose dehydrogenase is a very useful enzyme used widely in the assay of L-fucose (Agricultural and Biological Chemistry, 39, 2227–2234, 1975 and Journal of Biochemistry, 86, 1559–1565, 1979).

Methods for the purification of L-fucose dehydrogenase from the liver of mammals are not very practical because of the small amounts and small yields obtained. Methods in which microorganisms are cultured for the production of L-fucose dehydrogenase require the induction of the enzymatic production of expensive sugars such as L-fucose and D-arabinose. Thus, a less expensive method for the production of L-fucose dehydrogenase is desired.

L-fucose dehydrogenase is widely distributed, being found in hepatocytes, bacteria, actinomycetes, and basidiomycetes, and, as mentioned before, there are a number of published methods for its enzymatic purification. However, the structure of the gene coding for L-fucose dehydrogenase is unknown, as is the sequence of amino acids in this enzyme, so there are no known methods for the production of L-fucose dehydrogenase by genetic engineering.

The object of this invention is to obtain an isolated gene of L-fucose dehydrogenase, to create new microorganisms (particularly, new strains of *Escherichia coli*) harboring a plasmid that carries the L-fucose dehydrogenase gene and suitable for industrial production of said L-fucose dehydrogenase, and to provide a process for producing L-fucose dehydrogenase by using said new microorganism.

Briefly, the first aspect of this invention relates to the gene of L-fucose dehydrogenase. The second aspect of this invention relates to new microorganisms harboring a plasmid into which an L-fucose dehydrogenase gene has been integrated. The third aspect of this invention relates to a process for producing L-fucose dehydrogenase, which comprises cultivating said new microorganism and recovering L-fucose dehydrogenase from the culture.

Below, this invention will be explained in detail.

Known methods described below can be used for the cloning of DNA that codes for L-fucose dehydrogenase.

First, for example, DNA can be isolated from microorganisms that can produce this enzyme. The DNA obtained can be cleaved with restriction enzymes, the DNA fragments obtained can be ligated with plasmids or a phage vector, and the ligated fragments can be introduced into host cells and used to prepare a genomic DNA library.

To screen for clones that contain a gene that codes for the L-fucose dehydrogenase being sought from this genomic DNA library, part of the amino acid sequence of L-fucose dehydrogenase should first be identified, and then this sequence should be synthesized with a DNA synthesizer. For the identification of the partial amino acid sequence, first, purified L-fucose dehydrogenase should be hydrolyzed with a protease highly specific for a particular amino acid residue, and the hydrolyzed peptides obtained should be isolated by reversed-phase HPLC. The amino acid sequences of these peptides are identified by Edman degradation. There are two methods by which a synthetic DNA probe can be designed based on these amino acid sequences. In one method, all of the combinations of the sequences can be synthesized. In the other method, long oligonucleotides can be synthesized with use of the codons of high frequency that have been identified so far.

In the procedure of screening of the library with a DNA probe, first, plating is done, and the colonies or plaques that grow are transferred to a nitrocellulose or nylon filter, and the DNA is denatured and fixed to the filter. The filter is incubated in a solution that contains a DNA probe labelled with $^{32}P$, and the DNA fixed on the filter hybridizes with the probe DNA (hereinafter, this step will be referred to as "hybridization"). The incubation temperature should be at about the melting temperature, Tm, of the probe. After the hybridization, nonspecifically bound substances were removed by washing, and clones with which the probe hybridized were identified by autoradiography. Clones were isolated by this procedure being repeated, and analyzed as follows.

When the recombinants were *Escherichia coli* cells, they were cultured on a small scale in test tubes or the like, and plasmids were extracted by the usual methods, and cleaved by restriction enzymes before being studied by agarose or acrylamide gel electrophoresis to find if cloned insertion fragments were being produced. The electrophoretic pattern was transferred to a nitrocellulose or nylon membrane, and hybridized as described above before being tested to find if insertion fragments had hybridized with the DNA probe. In the final step, the base sequence of the insertion fragments was identified by well-known methods. When the recombinants were phages, analysis of the clones was done by basically the same steps. Cloned phages were used to infect host-cell E. coli being cultivated, and phage DNA was obtained from the culture broth. Details of the method for the purification of phage DNA are given in, for example, Course in Biochemical Experimentation, vol. 1, as "Method II for genetic research", on page 100 (Tokyo Kagaku Dojine Co. Ltd., Tokyo), 1986. As described there, phages are grown in culture, and after being purified, their DNA is isolated and purified, and the phage DNA obtained is cleaved with restriction enzymes and separated by gel electrophoresis to find insertion fragments. Hybridization with probe DNA is searched for. Finally, the base sequence of the insertion fragments is identified, to check for cloning.

From the base sequence, the primary structure of L-fucose dehydrogenase is deduced, and analysis of the N-terminal, the amino acid composition, partial amino acid sequences, and the molecular weight of the purified L-fucose dehydrogenase can be done to find the structure of the gene and the sequence of the amino acids for this enzyme.

It is possible to insert the structural gene for L-fucose dehydrogenase obtained in this way into suitable host cells, such as E. coli cells that can express this enzyme, by ligation of the structural gene with an expression vector, and by its introduction into said host cells; by their culture, it is possible to produce polypeptides with L-fucose dehydrogenase activity.

The desired expression can be checked for by measurement of L-fucose dehydrogenase activity. For example, in an assay mixture for L-fucose dehydrogenase that contains L-fucose and β-nicotinamide adenine dinucleotide (NAD+), a cell extract of the recombinant E. coli cells or the like can be added. The reduction of NAD+ at this time can be measured as the additional absorbance at 340 nm, as measured with a spectrometer, from which result the activity of L-fucose dehydrogenase can be calculated.

L-fucose dehydrogenase can be purified by chromatography of the transformants. The cultured cells can be disrupted, and the supernatant can be obtained. This supernatant can be treated by ion-exchange chromatography, gel filtration, hydrophobic chromatography, etc., to give the desired peptide.

As described above, this invention provides a method for the production by genetic engineering of L-fucose dehydrogenase, the primary structure and amino acid sequence of which are disclosed herein.

Next, the invention will be explained further with reference to the following examples, but this invention is not to be taken to be limited to these examples.

EXAMPLE 1

Cloning of structural gene of L-fucose dehydrogenase.

Isolation and Purification of Genomic DNA:

First, cells of *Arthrobacter oxidans* F1 (FERM BP-3674), which produces much L-fucose dehydrogenase activity, were used to inoculate 750 ml of a culture broth of 0.5% yeast extract, 1.0% peptone, 0.3% $KH_2PO_4$, and 0.1% $MgSO_4 \cdot 7H_2O$, pH 7.0, and were cultured at 30° C. for 24 hours. Then the culture broth was centrifuged to harvest the cells, which were suspended in 10 ml of a lysozyme buffer (100 mM Tris-HCl, 100 mM EDTA, 20 mg/ml lysozyme, pH 7.0), and the suspension was kept for 30 min at 0° C. To the suspension, 5 ml of extraction buffer (50 mM Tris-HCl, 0.5% SDS, 0.1M EDTA, and 1 mg/ml proteinase K, pH 7.5) was added, and the mixture was kept at 50° C. for 2 hours. To the mixture was added the same volume of phenol saturated with TE buffer (10 mM Tris-HCl and 1 mM EDTA, pH 8.0), and the mixture was stirred gently and centrifuged for 15 minutes at 3000 rpm. The upper layer was collected. Below, this procedure is called "phenol extraction". The upper layer was dialyzed against TE buffer, and ribonuclease A was added to the final concentration of 20 µg/ml. The mixture was incubated at 37° C. for 1 hour, phenol extraction was done, and dialysis against TE buffer was repeated. By the steps described below, 10 mg of genomic DNA was obtained.

Preparation of a Genomic DNA Library:

Some 30 µg of the genomic DNA obtained was digested with 250 units of the restriction enzyme EcoRI at 37° C. for 6 hours, and an amount corresponding to 10 µg of the digest was treated on 0.7% agarose gel electrophoresis. After the electrophoresis, Southern blotting (Method II for Genetic Research II, above, pp. 218-221) was done to transfer the DNA to a nylon membrane (Hybond-N+, Amersham).

A part of the amino acid sequence of L-fucose dehydrogenase was deduced, and the 20-base sequence shown as sequence of SEQ ID No. 1 in the sequence listing was synthesized on a DNA synthesizer, for use as a hybridization probe.

To identify a partial amino acid sequence, 5 nmol of the purified L-fucose dehydrogenase obtained for *A. oxidans* was digested with 50 pmol of the protease trypsin for 15 hours at 37° C., and the digest was separated and purified by HPLC with a butyl silica column, and the sequence of some of the fractions were identified on a gas-phase peptide sequencer (Applied Biosystems 477A). The amino acid sequence identified was that shown as sequence of SEQ ID No. 2 in the sequence listing.

Next, 50 ng of synthesized DNA was labelled with $^{32}P$ with a Megalabel kit (Takara Shuzo). All of the probe obtained was incubated overnight at 55° C. for hybridization in about 20 ml of a solution that contained 6×SSC (1×SSC contains 8.77 g of NaCl and 4.41 g of sodium citrate in a total volume of 1 liter), 1% SDS, 100 µg/ml herring sperm DNA, 5×Denhardt's (bovine serum albumin, poly(vinylpyrrolidone), and Ficoll, each at the concentration of 0.1%), with use of the filter that was prepared as described above. Then the filter was washed at room temperature in 6×SSC for 10 minutes, and twice at 50° C. in 2×SSC containing 0.5% SDS for 10 minutes. After removal of excess water, the filter was used for autoradiography overnight at −70° C. with intensifying screens. Probe hybridization was found at the position of a size of about 5 kb.

Some 20 µg of the remaining DNA that had been digested with EcoRI was treated by 0.7% agarose gel electrophoresis, and the region corresponding to a size of 4.4 to 6.6 kb was cut out extracted, and purified with an EASYTRAP kit (Takara Shuzo). Half of the DNA fragments obtained were mixed with 0.5 µg of λgt11-EcoRI arms (Stratagene), and ligation was done with a ligation kit (Takara Shuzo), followed by packaging with a Gigapack Gold kit (Stratagene), which resulted in a genomic library.

Identification and Isolation of Positive Clones:

With *E. coli* Y1090 as host cells, the genomic DNA library of *A. oxidans* was plated in five rectangular plates measuring 14×10 cm, so that about 400 plaques grew on each plate. To do this, *E. coli* Y1090 cells were grown overnight at 37° C. in L broth containing 0.4 mg/ml maltose. Then 0.2 ml of this culture broth was mixed with 0.1 ml of the phage solution and the mixture was incubated for 15 minutes at 37° C. To this, 8 ml of soft agar (L medium to which agarose had been added to the final concentration of 0.6%, and then autoclaved, after which the mixture was kept at 50° C.) was added, and the mixture was spread on rectangular plates on the top of L medium, and allowed to cool, after which the plates were kept at 37° C. for 10 hours to allow the formation of phage plaques (herein-after, this procedure is referred to "plating").

Next, two hybridization filters were prepared from each of these plates. To do this, a nylon membrane was placed on the surface of the plate for 30 seconds, and the membrane was then placed on paper that had been immersed in a solution of 0.5M NaOH and 1.5M NaCl for 5 minutes (for denaturation), and on paper that had been immersed in a buffer of 0.5M Tris-HCl (pH 7.0) that contained 1.5M NaCl (for neutralization). The membrane was then washed in 2×SSC. (hereinafter, this procedure is referred to as "filter treatment"). For the second filter, the time of contact between the plate and the nylon membrane was 2 minutes. These filters were treated under the same conditions as described before for hybridization, and 65 positive signals were found.

From among these signals, four suitable plaques that correspond to the signals were selected, and were recovered from the agar in 0.2 ml of SM solution (which was prepared from 5.8 g of NaCl, 2 g of MgSO$_4$·7H$_2$O, 50 ml of 1M Tris-HCl buffer, pH 7.5, and 5 ml of 2% gelatin dissolved in water and made to a total volume of 1 liter). A suspension was made and the suspension was diluted appropriately and plated by the procedure described above to give about 300 plaques in round dishes with a diameter of 9 cm. It was possible to isolate single plaques among the four plaques. These clones were named $\lambda_{FDH}$F1-F4.

Preparation of λ-DNA:

Liquid culture of *E. coli* Y1090 cells as host cells for the cloned phages was done to prepare phage DNAs (Method II for Genetic Research, above, page 100). To do this, the phase solution was used to infect the host cells, the cells were disrupted and polyethylene glycol 6000 and NaCl were added to the culture supernatant and phage particles were collected by precipitation. These phage particles were suspended in TE buffer and extracted with phenol to obtain purified phage DNA. From 100 ml of culture broth, about 100 μg of DNA was obtained.

Identification of Insertion Fragments and their Isolation and Purification:

A 10 μg portion of each of the DNAs prepared as above was digested with 50 units of EcoRI for 2 hours. Then 1/20th of this reaction mixture was treated by electrophoresis on a 1.0% agarose gel, and the insertion fragments were identified. It was found that $\lambda_{FDH}$F1-F4 were all cloned, and that a fragment 5.3 kb long had been inserted in each.

Next, the remaining reaction mixture from the EcoRI digestion was treated by electrophoresis on 1.0% agarose gel, and the portions of the gel containing the desired insertion fragment was cut out and extracted with an EASYTRAP kit.

Identification of Restriction Sites of the Insertion Fragments:

The insertion fragments obtained were digested with a number of restriction enzymes and the digestion products were treated by electrophoresis. The electrophoretic pattern of the cleaved fragments were analyzed. BamHI, SphI, PstI, and SalI sites were found to be the restriction sites. Southern blotting was used to transfer DNA from the agarose gel to a nylon membrane (Amersham), and hybridization was done to find which cleaved fragments coded for L-fucose dehydrogenase. The desired fragment was identified in each of the four clones as a 2.7 kb DNA fragment cleaved from a 5.3 kb insertion fragment with BamHI.

Identification of Base Sequence:

The 2.7 kb BamHI-EcoRI fragment from $\lambda_{FDH}$F1 was isolated and purified as described above. Next, it was treated with a DNA blunting kit (Takara Shuzo) to give it blunt ends, and was cloned into the HincII site of M13mp19RF DNA.

Figure 1:
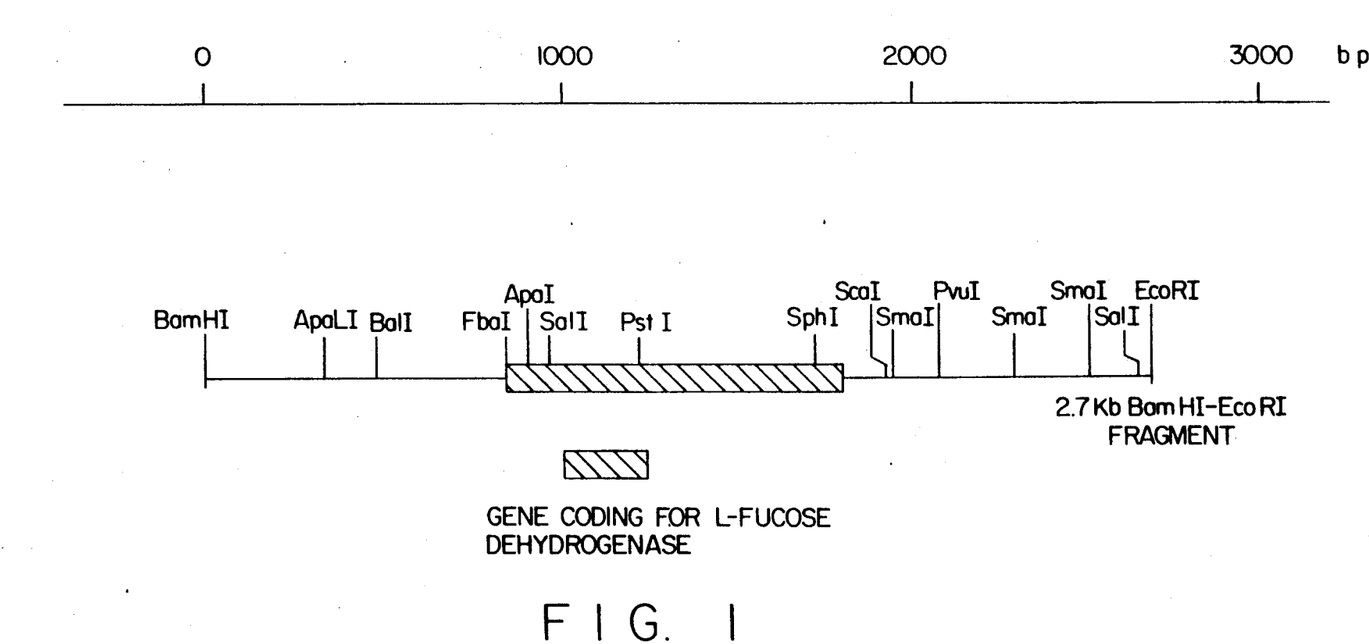
FIG. 1 shows the restriction map of BamHI-EcoRI fragment, 2.7 kb, and position of the gene coding for L-fucose dehydrogenase.

The recombinant M13mp19RF DNA was digested with XbaI and SacI, and mutants were prepared by the exonuclease III method (Method for Genetic Research, pp. 186-200), with about 300 bp at a time being deleted from the XbaI site. Deletion mutants were prepared in the same way from recombinant M13mp19RF DNA that had the insertion fragment inserted with the opposite orientation. Then *E. coli* JM109 cells were transformed with the different M13mp19 derivative DNAs. Single-stranded DNA from M13mp19 derivatives was prepared and the base sequence of a 2.7 kb BamHI-EcoRI fragment was identified by the dideoxy method. An open reading frame 966 bp long was found in the fragment. The sequences identified before from the trypsin digest of L-fucose dehydrogenase were all coded for by this open reading frame. In this way, the complete base sequence coding for L-fucose dehydrogenase and the primary sequence of the enzyme were identified. FIG. 1 shows the restriction map of the 2.7 kb BamHI-EcoRI fragment, and the position of the gene coding for L-fucose dehydrogenase, and sequence of SEQ ID No. 3 in the sequence listing shows the complete base sequence of the 2.7 kb fragment, which contains the base sequence that codes for L-fucose dehydrogenase, and the amino acid sequence of L-fucose dehydrogenase shown below.

EXAMPLE 2

Construction of a plasmid that expresses the L-fucose dehydrogenase peptide

From the M13mp19 derivatives for which the base sequence was identified, derivative lacking the sequence up to residue 32 upstream of the initiation codon for the L-fucose dehydrogenase region was obtained. This derivative had the base sequence shown as sequence of SEQ ID No. 4 in the sequence listing, starting at the EcoRI site in the multicloning site of M13mp19, which is the sequence 5'-GAA TTC GGG ACA GGC CCC CAA CCA GGA GAA AGA CTG ATC-3', from the initiation codon ATG upstream. The sequence GAA TTC G on the 5' end is from M13mp19, and the remainder of the sequence is from the genomic DNA of

*A. oxidans*. This EcoRI site and the ScaI site downstream from the L-fucose dehydrogenase gene were cleaved giving a fragment about 1100 bp long. The fragment was given blunt ends by use of a DNA blunting kit. Plasmid pTV119N (Takara) was cleaved at the NcoI site for use as a vector, and the ends were blunting with use of the DNA blunting kit. Then the fragment prepared above was inserted, giving plasmid pTFDH101. This plasmid coded for a polypeptide that had the N-terminal 322 amino acids of L-fucose dehydrogenase plus the sequence of 14 amino acids shown as sequences of SEQ ID No. 5 in the sequences listing. The plasmid pTFDH101 was introduced into *E. coli* JM109 cells, and the cells obtained were designated *E. coli* JM109/pTFDH101 cells.

Next, the plasmid pTFDH101 was inserted into *E. coli* GM33 cells lacking dam methylase, and the recombinants were cultured, and plasmid DNA was prepared from them. This plasmid DNA was cleaved with the restriction enzymes NcoI and FbaI. In the presence of dCTP, Klenow fragment was used to add one base and the ends were blunted with S1 nuclease. The fragments obtained gave plasmid pTFDH213 by self-ligation. This plasmid directly expressed the polypeptide with 322 amino acids of L-fucose dehydrogenase, shown in SEQ ID No. 3 in the sequence listing.

pTFDH213 was introduced into *E. coli* JM109 cells, and the cells obtained were designated *E. coli* JM109/pTFDH213, and deposited at the Fermentation Research Institute, Agency of Industrial Science and Technology, Japan, under the accession number of FERM BP-3675.

EXAMPLE 3

Expression of L-fucose dehydrogenase peptide by *E. coli*

Cells obtained as described in Example 2 of either *E. coli* JM109/pTFDH101 or *E. coli* JM109/pTFDH213 were used to inoculate 5 ml of L medium containing 100 µg/ml ampicillin, which was cultured at 37° C. by shaking culture. When the absorbance reached an O.D.$_{600}$ of 0.5, isopropyl-1-thio-β-D-galactopyranoside was added to the final concentration of 1 mM, and the mixture was incubated overnight at 37° C. Then the cells were harvested by centifugation of the culture broth and suspended in 20 ml of 50 mM phosphate buffer, pH 8.0. The cells were disrupted by ultrasonic treatment and centrifuged. The supernatant was obtained and called the cell extract. The L-fucose dehydrogenase activity of the cell extract was assayed as follows. The reaction mixture for the assay contained 1.0 ml of 30 mM L-fucose, 5 mM $KH_2PO_4$ in 1.8 ml of a buffer of glycine-sodium hydroxide (pH 8.0), 0.1 ml of 15 mM NAD, and 0.1 ml of the cell extract, suitably diluted. The reaction mixture was kept at 37° C. for 10 minutes, and then its absorbance at 340 nm was measured (this was called the O.D. sample). As a control, 0.1 ml of distilled water was used instead of the cell extract, and the absorbance of this mixture was measured (this was called the O.D. of the blank).

The L-fucose dehydrogenase activity was calculated from the $\Delta O.D._{340}$, which was the O.D. of the sample minus the O.D. of the blank, as shown in the following Equation I.

$$\text{Units of activity/milliliter} = \frac{\Delta O.D._{340} \times 3.0 \text{ (ml)}}{6.22 \times 10 \text{ (min)} \times 0.1 \text{ (ml)} \times d} \times df \quad [I]$$

where 6.22 is the millimolar extinction coefficient of NADH at 340 nm, d is the length of the light path (cm), and df is the dilution.

The assay showed that 20 ml of the cell extract prepared as described above had about 30 units of L-fucose dehydrogenase activity. When *E. coli* JM109 cells not carrying the plasmid were treated in the same way, no L-fucose dehydrogenase activity was detected.

As described above, this invention discloses the amino acid sequence of L-fucose dehydrogenase and the base sequence that codes for this enzyme, and also provides a convenient method by which the L-fucose dehydrogenase polypeptide can be prepared industrially by the methods of genetic engineering. With this invention, it is not necessary to use L-fucose to induce the enzyme, and productivity is high. In addition, by construction of a probe and primer based on this base sequence, it is possible to assay L-fucose dehydrogenase and to evaluate the extent of its expression. With this invention, it is also possible to produce antibodies based on the amino acid sequence of the enzyme.

---

What we claim is:

1. An isolated gene from *Arthrobacter oxidans* encoding L-fucose dehydrogenase.

2. *Escherichia coli* containing a plasmid which comprises an isolated gene from *Arthrobacter oxidans* encoding L-fucose dehydrogenase.

3. Process for producing L-fucose dehydrogenase which comprises cultivating *Escherichia coli* containing a plasmid that carries an isolated L-fucose dehydrogenase gene from *Arthrobacter oxidans* to produce the L-fucose dehydrogenase and recovering the L-fucose dehydrogenase from the culture.

* * * * *